(12) United States Patent
Deininger et al.

(10) Patent No.: US 8,082,037 B2
(45) Date of Patent: Dec. 20, 2011

(54) FORM FOR RETAINING BATTERY IN IMPLANTABLE MEDICAL DEVICE

(75) Inventors: Steve T. Deininger, Blaine, MN (US); Charles E. Peters, Blaine, MN (US); Jeffrey J. Clayton, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 579 days.

(21) Appl. No.: 11/776,746

(22) Filed: Jul. 12, 2007

(65) Prior Publication Data

US 2009/0018600 A1   Jan. 15, 2009

(51) Int. Cl.
*A61N 1/375* (2006.01)
(52) U.S. Cl. .......................................................... 607/36
(58) Field of Classification Search .................... 607/36
See application file for complete search history.

(56) References Cited

U.S. PATENT DOCUMENTS

| | | | |
|---|---|---|---|
| 6,721,602 B2 | 4/2004 | Engmark | |
| 7,123,966 B2 | 10/2006 | Deininger | |
| 2003/0040779 A1 | 2/2003 | Engmark | |
| 2004/0127952 A1 | 7/2004 | O'Phelan | |
| 2005/0149140 A1* | 7/2005 | Hansen et al. | 607/37 |
| 2005/0154423 A1 | 7/2005 | Goedeke | |

FOREIGN PATENT DOCUMENTS

WO   WO 2005/110539   * 11/2005

OTHER PUBLICATIONS

PCT Search Report and Written Opinion dated Sep. 22, 2008.

* cited by examiner

*Primary Examiner* — Scott Getzow
(74) *Attorney, Agent, or Firm* — Scott A. Marks; Campbell Nelson Whipps, LLC

(57) ABSTRACT

A form for retaining a battery in implantable medical device includes outer edge and first and second opposing major surfaces. The first major surface of the form includes a recess, a ridge disposed between the recess and the outer edge, and a trough forming element disposed between the ridge and the outer edge. The ridge is configured to engage at least a portion of a major surface of the battery retained in the form. The trough forming element has first and second edge surfaces positioned to engage an edge surface of the retained battery to form a trough configured to receive adhesive. The recess is disposed adjacent the ridge and is configured to allow for expansion of the retained battery during recharge. The retention assembly is configured to secure the first major surface of the battery against the ridge to prevent adhesive from leaking from the trough into the recess.

17 Claims, 14 Drawing Sheets

FORM FOR RETAINING BATTERY IN IMPLANTABLE MEDICAL DEVICE

FIELD

This disclosure relates, inter alia, to implantable medical devices. More particularly, it relates to forms or cups for retaining components of medical devices.

BACKGROUND

Many implantable medical devices, such as infusion devices, neurostimulators, pacemakers and defibrillators, include multiple components disposed within a hermetically sealed housing to protect the components from the environment of the human body. Placement of the components within the housing is important from both manufacturing and functional perspectives. For example, it is desirable for the components to be placed in the housing in a space efficient manner so that the overall size and volume of the device is kept small for purposes of patient comfort. In addition, the number of steps required in the manufacture of an implantable medical is a concern, as each step requires careful attention, and time. Efforts to reduce or simplify the complexity, cost, and time of manufacturing and the assembly process directly impact the cost of the implantable medical device for patients. More simple and cost-effective device assembly processes for implantable medical devices are desirable.

One development that has reduced the size of implantable medical devices is the use of rechargeable batteries. Larger cells are needed if the batteries are not rechargeable to provide sufficient power to operate the device over an extended period of time. With rechargeable batteries, small cells that deplete more rapidly may be employed, as they can be recharged. However, rechargeable batteries present some manufacturing design concerns. For example, rechargeable batteries expand during the recharging process, and room for such expansion should be accounted for in the design. In addition, expansion and contraction of the battery during use may cause the battery to come loose or compromise its electrical connections unless adequately accounted for in the device design.

SUMMARY

The present disclosure describes, inter alia, methods, systems and devices that employ a form for retaining components of an implantable medical device. In various embodiments, the form retains multiple components, reducing the number of steps for assembly of the implantable device. In various embodiments, the form securely retains a rechargeable battery, allowing for expansion and contraction without compromising mechanical or electrical connections of the battery.

In an embodiment, a form for retaining a battery in implantable medical device is described. The battery has first and second opposing major surfaces and an edge surface connecting the first and major surfaces. The form includes and outer edge and first and second opposing major surfaces. The first major surface of the form includes a recess, a ridge disposed between the recess and the outer edge, and a trough forming element disposed between the ridge and the outer edge. The ridge is configured to engage at least a portion of the first major surface of the battery retained in the form. The trough forming element has first and second edge surfaces positioned to engage the edge surface of the retained battery to form a trough configured to receive adhesive. The recess is disposed adjacent the ridge and is configured to allow for expansion of the retained battery during recharge. The retention assembly is configured to secure the first major surface of the battery against the ridge to prevent adhesive from leaking from the trough into the recess.

In an embodiment, a method for securing a battery in a form for insertion in a medical device is described. The form has an outer edge, a recess, and a ridge disposed between the outer edge and the recess. The method includes contacting at least a portion of a major surface of the battery to the ridge and pressing the at least a portion of the major surface of the battery against the ridge. The method further includes forming a trough between a side edge of the battery and a trough forming element of the form. The method also includes placing adhesive in the trough. The battery is pressed against the platform with sufficient force to prevent the adhesive from leaking from the trough into the recess.

In an embodiment, a form for inserting in an implantable medical device is described. The form includes a battery retention region, a electronic circuitry retention region;, a recharge coil retention region, and a telemetry coil retention region.

By providing devices, systems and methods employing a form capable of retaining multiple components of an implantable medical device or capable of allowing battery expansion and contraction without compromising mechanical or electrical connections, the devices may be assembled with fewer steps and with improved integrity. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

The present disclosure describes, among other things, methods, systems and devices that employ a form for retaining components of an implantable medical device. In various embodiments, the form retains multiple components, reducing the number of steps for assembly of the implantable device. In various embodiments, the form securely retains a rechargeable battery, allowing for expansion and contraction without compromising mechanical or electrical connections of the battery.

Figure 1:
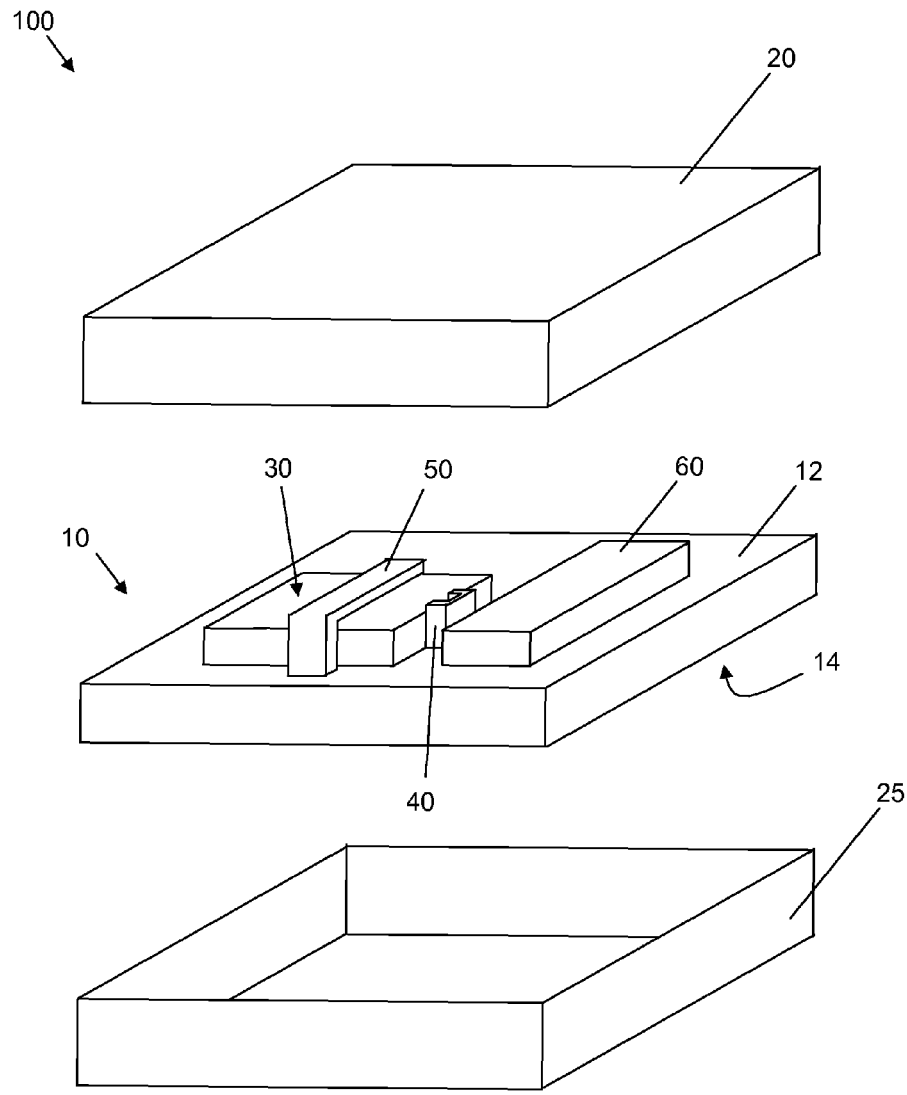
FIG. 1 is an exploded view of an illustrative implantable medical device showing a form retaining a battery and electrical circuitry.

FIG. 1 is an exploded view of an illustrative implantable medical device 100 showing selected components including form 10 and first second parts of housing 20, 25 or case of device 100. Device 100 may be any implantable medical device that employs a battery 30. For example, device 100 may be a device that provides therapy, such as an infusion device, a neurostimulation device, a pacemaker, a defibrillator, a cochlear implant, and the like; a monitoring device; and the like. Housing 20, 25 is typically made of metallic material and hermetically sealed by welding first 20 and second 25 parts together. Form is shaped and sized to be disposed within the sealed housing 20, 25. In various embodiments, form 10 is sized and shaped to mate or provide an interference fit with a portion of housing 25 or shield (not shown) to be disposed in the housing. Form 10 may be secured against housing 25 through an adhesive such as epoxy. The form 10 depicted in FIG. 1 is shown retaining a battery 30 and electrical circuitry 60. The battery 30 is electrically coupled (not shown in FIG. 1) to the electronics 60. An edge of the battery 30 and trough forming element 40 form a trough into which adhesive may be dispensed. This will be discussed in greater detail below. A retention assembly 50, which may consist of one or more parts, is also shown and facilitates retention of battery 30 relative to form 10. Retention assembly 50 and trough forming element 40 may be formed from form 10 or mechanically coupled (including coupling via adhesive) to form 10. As shown in FIG. 1, form has opposing first 12 and second 14 major surfaces.

Figure 2:
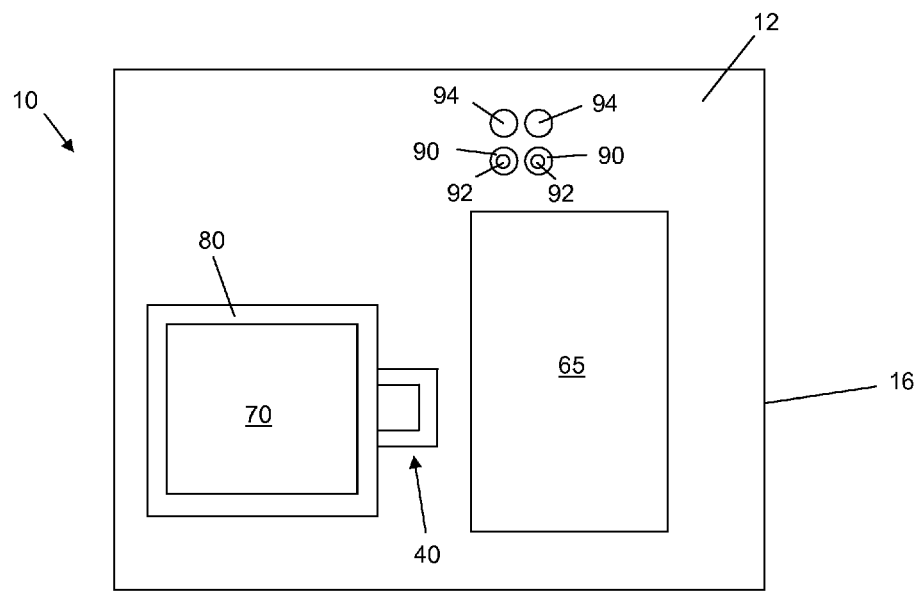
FIG. 2 is a top view of an illustrative form for insertion into a medical device.
Figure 3:
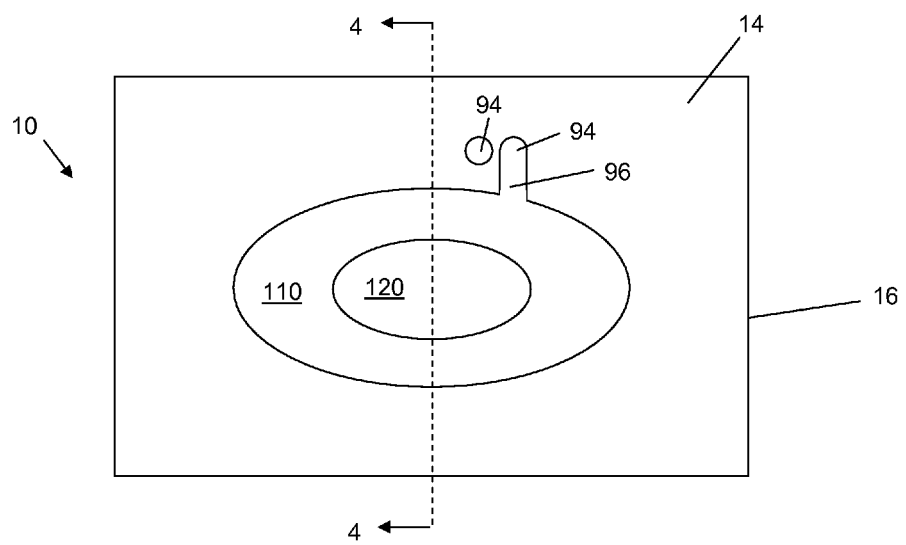
FIG. 3 is a bottom view of an embodiment of the form of FIG. 2.

Referring to FIGS. 2-3, top (FIG. 2) and bottom (FIG. 3) views of an illustrative form 10 for insertion into a medical device is shown. Form 10 includes a region 65 for receiving electronic circuitry, a recess 70 to allow for expansion of battery and a ridge 80 that engages a portion of a major surface of the battery. Ridge 80 is disposed between recess and outer edge 16 of form 10 and is elevated with respect to recess 70, but need not be elevated with regard to surrounding portions of the major surface 12 of the form 10. In the embodiment depicted in FIG. 2, ridge 80 defines the periphery or outer edge of the recess 70 and is continuous. It will be understood that a discontinuous ridge 80 will be sufficient to serve the purpose of providing a platform against which a portion of the battery may rest or be pressed.

Form 10 may include pin recesses 90 into which pins 92 may be molded or pressed.

Form 10 may also include holes 94 that extend from the first major surface 12 to the opposing second major surface 14. Ends of a coil, such as a recharge or telemetry coil (not shown in FIGS. 2-3) may be electrically coupled to pins 92 which may be electrically coupled to electrical circuitry. Ends from coil may be fed through holes 94 from second major surface 14 to first major surface 12 of form 10 to be coupled to, e.g. wrapped around, pins 94. Pins 92 may be formed or machined from any electrically conductive material. For example, pins 92 may be formed from nickel, nickel-colbalt ferrous based alloys such as kovar, or the like.

Figure 4:
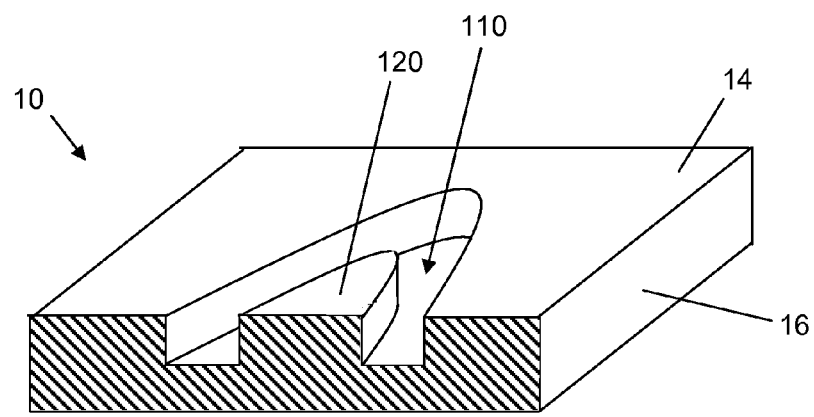
FIG. 4 is a perspective view of the form of FIG. 3 with a section taken through line 4-4.

Referring to FIG. 3, bottom surface 14 of various embodiments of form 10 includes a recess 110 for housing a coil. A raised portion 120 may also be included on bottom surface and may be formed from or attached to the form 10. In the embodiment depicted in FIG. 3, recessed portion 110 is disposed between raised portion 120 and outer edge 16. A channel 96 may be in communication with hole 94 and recess 110 to allow an end of a coil to be readily fed through hole 94 from bottom surface 14 to top surface 12 of form 10. In embodiments where coil is wound in a manner such that ends of coil emerge from opposing surfaces, channel 94 will facilitate feeding one end of coil wire through hole 94. The other end of coil wire may be fed trough a hole that is not in communication with a channel 96. Of course, any number of channels 94 may be present. Referring to FIG. 4, a perspective view of the form of FIG. 3 with a section taken through line 4-4. Recessed portion 110 and raised portion 120 are shown.

Figure 5:
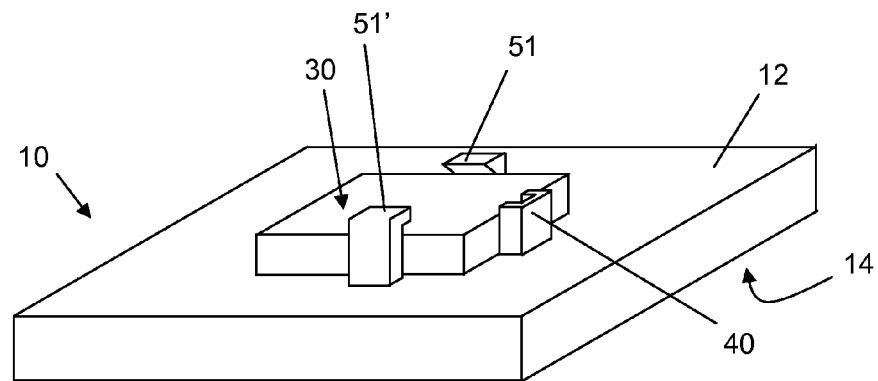
FIG. 5 is a perspective view of an illustrative form for insertion in an implantable medical device showing a retained battery.
Figure 6:
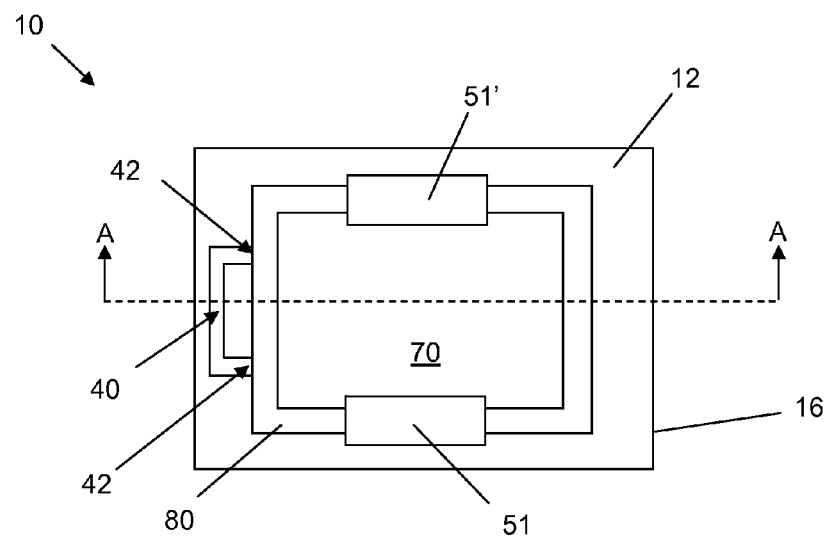
FIG. 6 is a top view of the form of FIG. 5.
Figure 7:
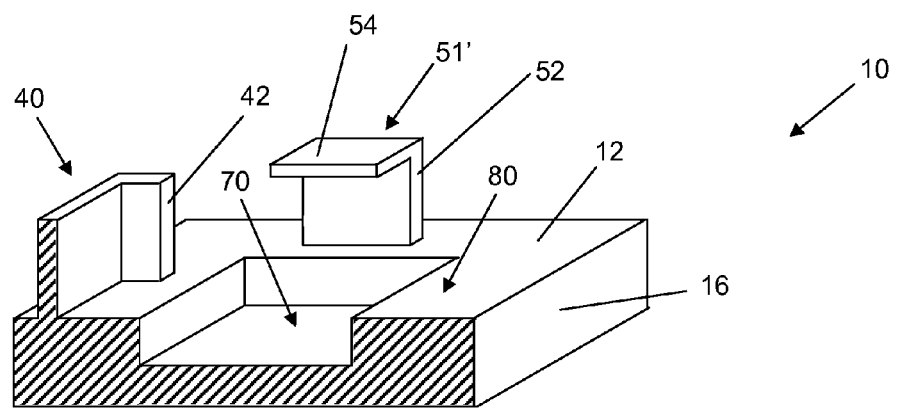
FIG. 7 is perspective view of the form of FIG. 6 with a section taken through line A-A.
Figure 8A:
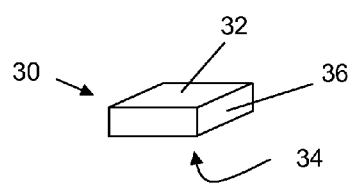
FIGS. 8A-C are perspective, top and bottom views, respectively, of a battery.
Figure 8B:
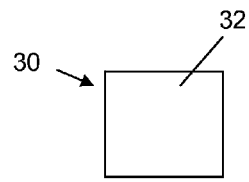
Figure 8C:
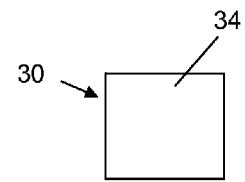
Figure 9:
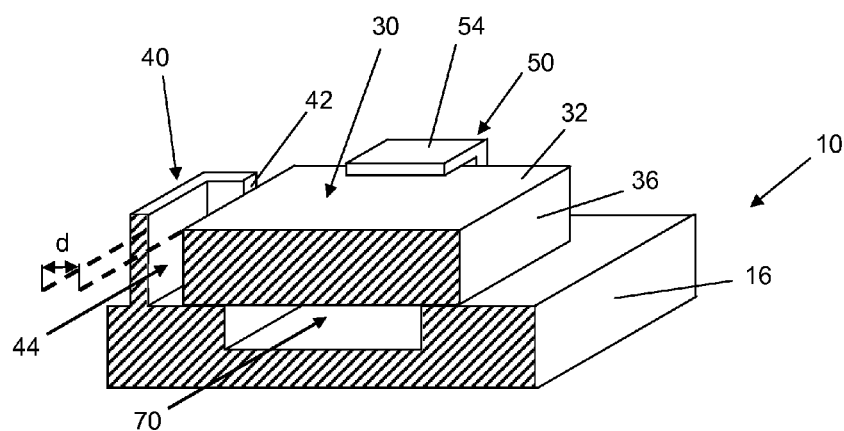
FIG. 9 is a top view of the form of FIG.6 with a section taken through line A-A showing a retained battery.
Figure 10:
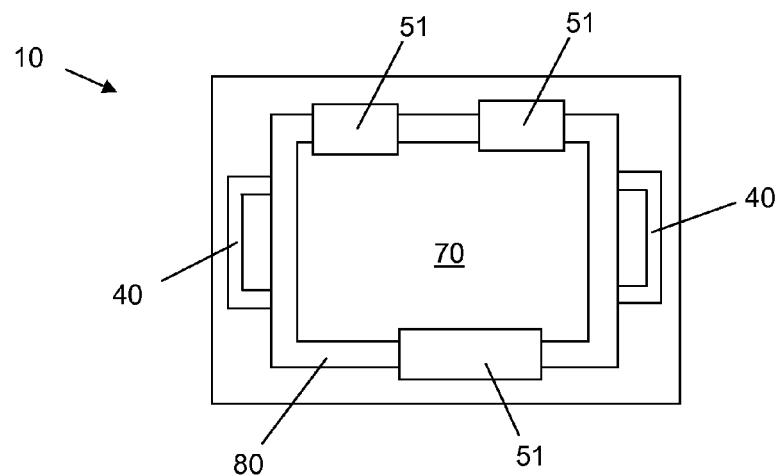
FIG. 10 is a top view of an illustrative form.

Referring to FIGS. 5-9, a form 10 for securing a battery 30 and a battery 30 are depicted. FIGS. 5-7 are a perspective view, a top view and a perspective view with a section through line A-A, respectively, of an illustrative form 10 for insertion in an implantable medical device. FIGS. 8A-C are perspective, top and bottom views of battery 30. FIG. 9 is the form of FIGS. 5-7 showing a retained battery with a section taken through line A-A. Form 10, which may consist of one or more parts, includes a trough forming element 40 having first and second edge surfaces 42 that engage an edge surface 36 of battery 30 to form a trough 44 into which adhesive may be dispensed. Any suitable adhesive may be used to adhere battery 30 to trough forming element 40. Examples of suitable adhesives include silicone RTV (room temperature vulcanization), and epoxy. Form 10 may include more than one trough forming element 40, the first and second side edges 42 thereof are configured to engage other portions of edge surface 30 of battery 30 to form an additional troughs 44. By way of example and referring to FIG. 10, form may include generally opposing trough elements 40 positioned such that edge surfaces engage generally opposing edge surfaces of the battery.

Referring back to FIGS. 5-9, form 10 in the depicted embodiment also includes a retention assembly including first 51 and second 51' engagement members. Retention assembly, in the case of FIGS. 5-7 engagement members 51, 51' collectively, is configured to secure at least a portion of a major surface 34 of battery 30 against ridge 80 to prevent adhesive from leaking through trough 44 into recess 70. In the depicted embodiment, first 51' and second 51 engagement members have walls 52 that are generally opposed and are positioned to engage or be in proximity of generally opposing edge surfaces 36 of battery 30. In the embodiment depicted in FIG. 5, battery 30 may be inserted at an angle against engagement member 51 and then pressed down towards engagement member 51', which can deflect to allow battery 30 to pass by engagement feature 54'. Engagement member 54' and associated wall 52 may also be deflected to release battery 30 from form 10.

Engagement members 51, 51' include engagement features 54 secured relative to engagement member wall 52 and positioned and configured to engage major surface 34 of battery 30. Engagement features 54 may exert force on a first major surface 32 of battery 30 such that a second opposing major surface 34 of battery 30 is pressed against ridge 80. Preferably, major surface 34 of battery is pressed against ridge 80 with sufficient force to prevent adhesive from leaking from trough 44 into recess 70. By way of example and referring to FIG. 10, a retention assembly may include any number of engagement members 51. Of course, any suitable retention assembly may be employed. In generally and referring back to FIG. 1, retention assembly 50 may include a strap, bar, hinge and lock, biasing member or any other suitable means for facilitating the retention of battery 30 and to sufficiently press major surface 34 of battery against ridge 80 to prevent adhesive from leaking from though 44 into recess 70. Holding the battery 30 with a retention assembly in combination with adhesive has been found to result in improved battery retention. It has further been found that troughs 44 with thinner depths (see, e.g., d in FIG. 9), for example less than about 0.01 inches, less than about 0.075 inches, or between about 0.04 and 0.06 inches, results in improved adhesion of battery 30 to trough forming element 40.

Figure 11A:
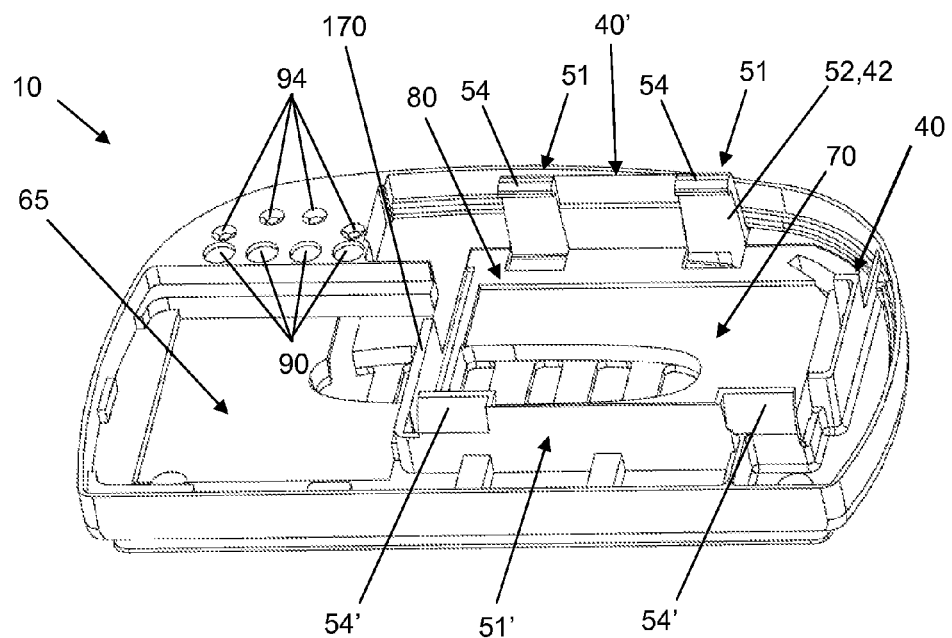
FIGS. 11A-C and 12A-B are perspective views of an embodiment of a form.
Figure 11B:
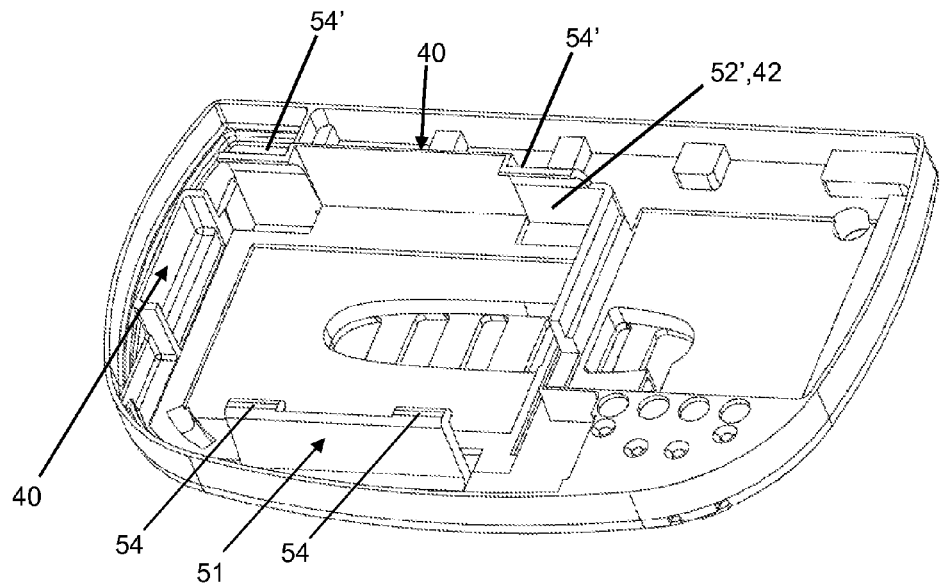
Figure 11C:
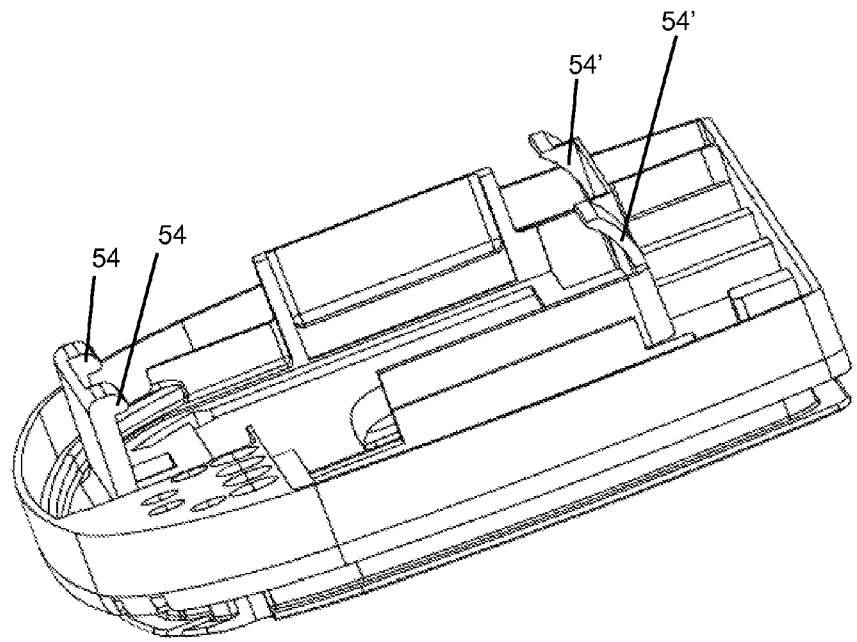

In FIGS. 11-13 a representative embodiment of a form 10 is shown. FIGS. 11A-C are perspective views in which first major surface 12 or portions thereof can be seen. The form 10 depicted in FIGS. 11A-C includes a recess 70, a ridge 80, and a plurality of trough forming elements 40. Some of the trough forming elements 40' are formed between engagement members 51 or are a part of engagement members 51. In such instances, a wall 54, 54' of the engagement member may serve as the side edge 42 of the trough forming element 40 that engages the battery to form the trough. Engagement member 51 may be considered as having two engagement walls 52, each with an engagement feature 54, 54'. Alternatively, a trough may be considered to be formed between two engagement members 51. The form 10 depicted in FIG. 11 also includes an additional feature 170 that serves to facilitate alignment of battery relative to ridge 80. Of course any number of additional features 170 may be employed to properly align a battery.

In the embodiment depicted in FIG. 11, engagement member 51' includes engagement walls 52' and arcuate engagement features 54' protruding from engagement walls 52'. The arcuate shaped engagement features 54' allow for a insertion of a battery at an angle against engagement wall 52'. The opposing end of the battery, while the battery is engaged by wall 52', may be pressed downwardly against opposing engagement features 54, the tops (the surface against which bottom surface 34 of battery is pressed) of which are curved to allow easier passage of battery. The opposing surface of the engagement features 54 is generally flat and protrudes from wall 52 at roughly at right angle to secure battery once it clears engagement feature 54. Engagement feature 54 and wall 52 deflect to allow passage of battery. When retained by the retention assembly (in the case of FIG. 11, engagement members 51, 51' collectively), edge surface 36 of battery (see, e.g., FIG. 8) contacts or is in close proximity to engagement member walls 52, 52', which also serve as side edges 42 of trough forming elements 40.

Figure 12A:
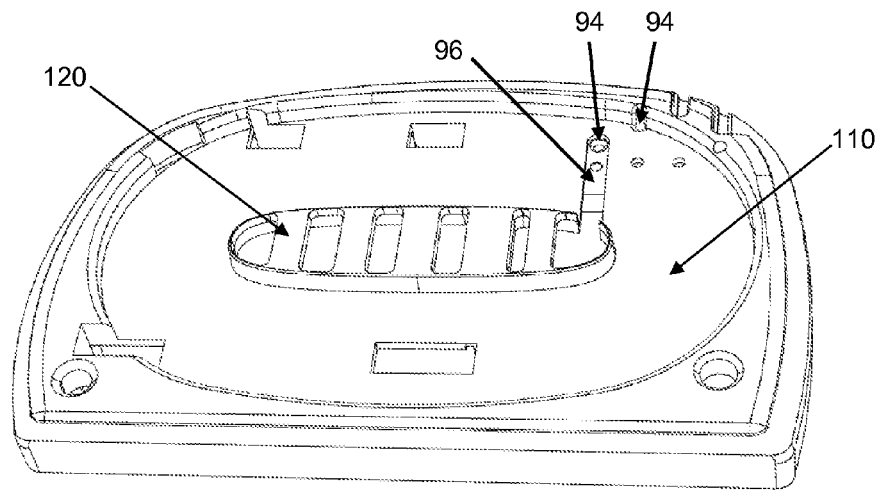
Figure 12B:
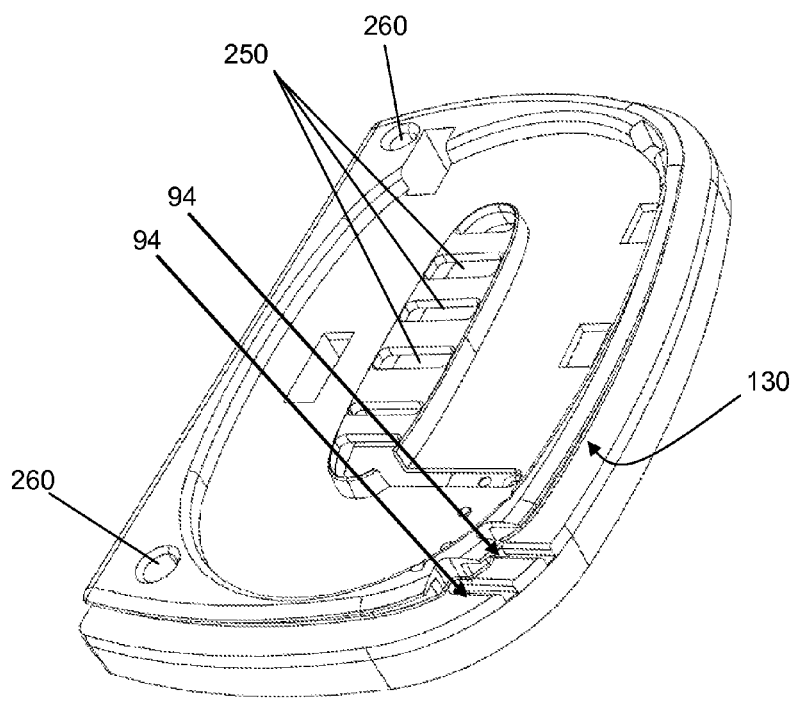

The form 10 depicted in FIG. 11 also includes a region 65 for receiving electronic circuitry, recesses 90 for receiving pins and holes 94 that extend to second major surface 14 of form 10, as shown in FIGS. 12A-B. As shown further shown in FIGS. 12A-B, form 10 also includes a raised portion 120 surrounded by a recessed portion 110 for receiving a coil, such as a recharge coil. A channel 96 in the recessed region 110 is in communication with a hole 94 to allow a wire from an end of coil to be feed through to opposing surface of form 10 and coupled to a pin. As shown in FIG. 12B, form 10 may contain a second recessed area 130 for receiving a second coil, such as a telemetry coil. Holes 94 are positioned to allow wires from an end of the second coil to be feed through to opposing surface of form 10 to be coupled to pins. As further shown in FIG. 12B, raised portion 120 of bottom surface of form 10 may include openings 250 to allow adhesive dispensed in device housing to flow (prior to curing) when bottom surface of form 10 is placed or pressed into device housing. The openings 250 allow for improved adhesion of form 10 to device housing. Bottom surface of form may also include further openings 260 to serve a similar function.

Figure 13A:
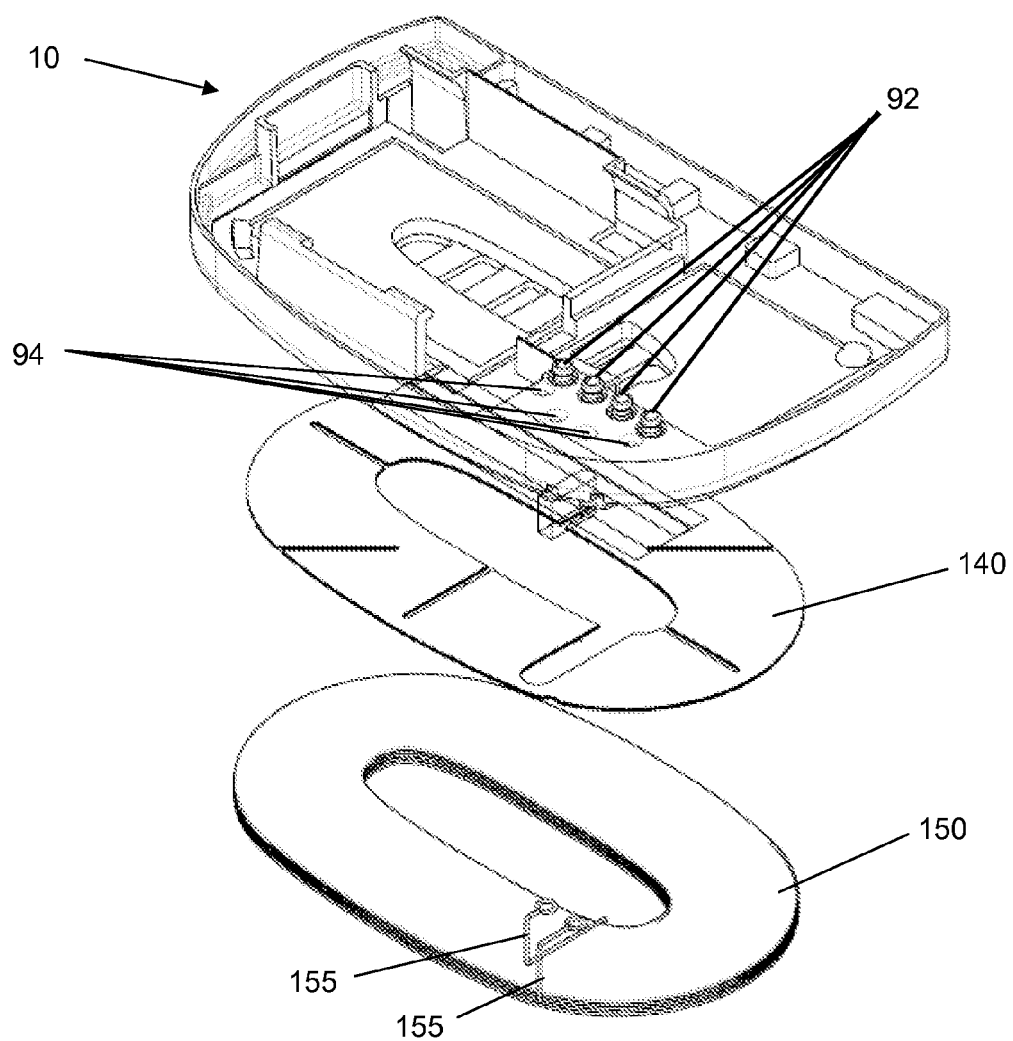
FIGS. 13A-B are exploded perspective views of the form of FIGS. 11 and 12 showing coils and other components that may be retained by the form.
Figure 13B:
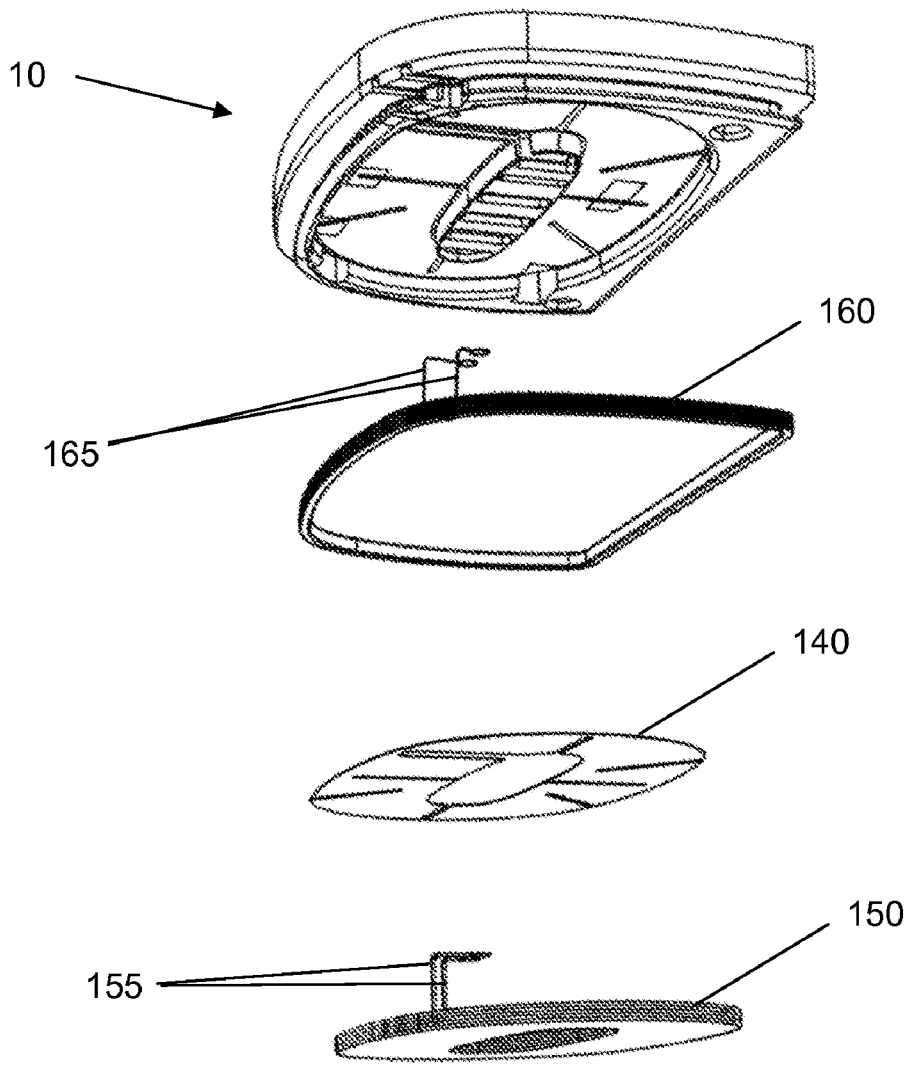
Figure 14:
FIG. 14 is a schematic cross section of a portion of a form with an attached coil and magnetic shielding.

FIGS. 13A-B are exploded views of forms 10 showing first 150 and second coils 160. FIG. 13A shows a recharge coil 150 and a magnetic shield 140. Recharge coil 150 is typically made of a thin wire having a diameter of about 0.01 inches and made of a copper material, such as magnet wire. The magnetic shield 140 may include any suitable shielding material, such as Metglas®. In the embodiment shown in FIG. 13A, magnetic shield contains laser cuts to reduce eddy currents. Coil 150 and magnetic shield 140 may be coupled to form 10 via any suitable attachment mechanism. For example and referring to FIG. 14, where a cross section of a portion of coil 150 and magnetic shield 140 is shown, shield 140 may be attached to form 10 via a layer of pressure sensitive adhesive 190. A layer of protective material 180, such as polyimide, may optionally be disposed between coil 150 and shield 140 to protect coil 150 from sharp edges of the shield 140. Pressure sensitive adhesive 190 may be disposed between polyimide layer 180 and shield 140 and protective layer 180 and coil 150. The ends 155 of the coil 150 may be feed through holes 94 and be looped around pins 92. With reference to FIG. 13B, telemetry coil 160 may be disposed in second recess 130 (see FIG. 12B) and coil ends 165 may be fed through holes 94 and lopped around pins. Telemetry coil is typically made of thin wire having a diameter of about 0.04 inches and made of a copper material, such as magnet wire. It will be understood that the locations of the recharge coil 150 and the telemetry coil 160 may be interchangeable. That is, recharge coil 150 may be disposed in second recessed area 130 and telemetry coil 160 may be disposed in first recessed region 110 (see, e.g., FIGS. 12A-B).

Figure 15:
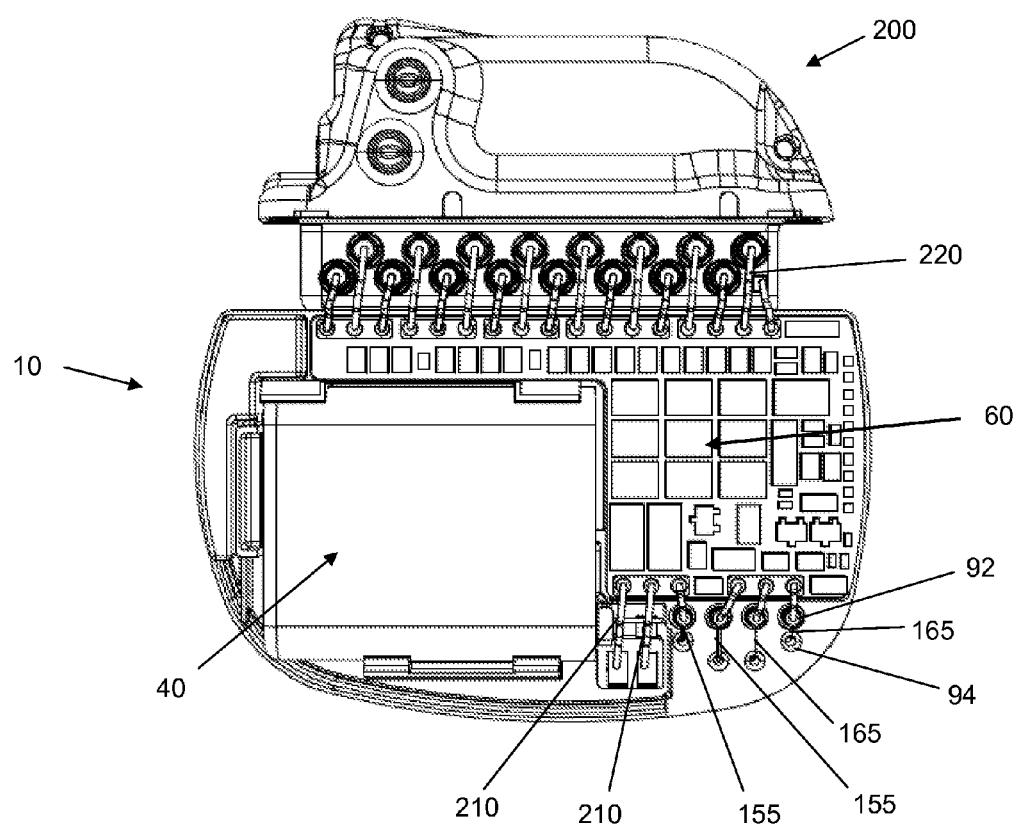
FIG. 15 is a side view of an embodiment of the form of FIGS. 11-13, showing retained battery and electronics and an illustrative connector header of an implantable neurostimulator.

Referring to FIG. 15 a side view of an embodiment of the form of FIGS. 11-13 is shown. A battery 30 and electronic circuitry 60 are disposed or retained in the form 10. Positive and negative terminals of battery 30 are operably coupled to electronic circuitry 60 via interconnects 210. Coils ends 155 of recharge coil and coil ends 165 of telemetry coil are operably coupled to electronic circuitry 60 via pins 92. In the embodiment depicted in FIG. 15, electronic circuitry is also operably coupled to a connector header 200 of an implantable neruostimulator via interconnects 220. Of course, electronic circuitry may be operably connected to output or input headers or elements of any suitable device.

Form 10 may be made of one or more pieces. Generally, form 10 is non-conductive and sufficiently rigid to maintain retained components, e.g. battery, electronic circuitry, and coils, in spatial orientation such that mechanical and electrical connections between components are not compromised. Examples of suitable materials for form 10 include liquid crystal polymer, with or without a suitable filler such as 30% glass, polyether ether ketone, and polyether amide. In various embodiments, form 10 is a single molded plastic form.

While it will be understood that a form, as described herein, may be suitable for retaining one or more components, there are advantages to form 10 being configured to retain multiple components. For example, a form 10 that contains regions for retaining or receiving a battery, electronic circuitry, a recharge coil and a telemetry coil serves to reduce manufacturing steps and increase the special integrity of the various components.

It will be understood that forms 10 and components thereof described above with regard to FIGS. 1-15 are but examples of forms 10 and components that may be employed to carry out the methods described below. However, for the sake of convenience, the discussion that follows with regard to the methods illustrated in the flow diagrams of FIGS. 16-17 will refer to components as described with regard to FIGS. 1-15. With regard to the methods described below, the form 10 has an outer edge 16, a recess 70, and a ridge 80 disposed between the outer edge 16 and the recess 70.

Figure 16:
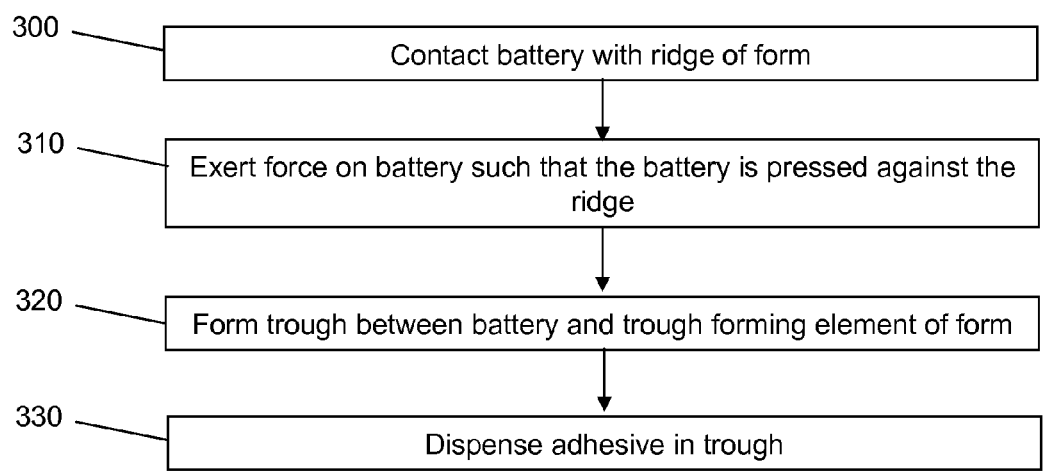
FIGS. 16-18 are flow diagrams of illustrative methods.

Referring to FIG. 16, a flow diagram of an illustrative method is shown. At least a portion of a major surface 34 of a battery 30 is contacted with the ridge 80 of the form 10 (300). Force is exerted on the battery 30 such that the at least a portion of the major surface 34 of the battery 30 is pressed against the ridge 80 (310). The battery 30 may be pressed against the ridge 80 by an engagement feature 54, 54' of the form 10. A trough 44 is formed between a side edge 36 of the battery 30 and a trough forming element 40 of the form 10 (320). Adhesive is then dispensed in the trough 40 (330). The battery 30 is pressed against the ridge 80 with sufficient force to prevent the adhesive from leaking from the trough 40 into the recess 70.

Figure 17:
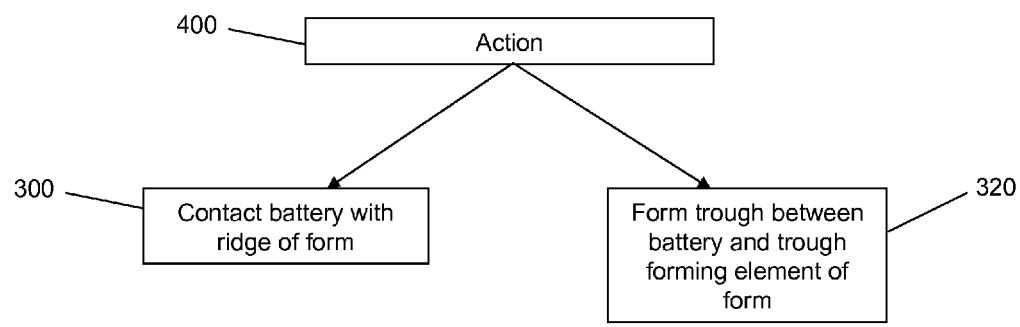

As shown in the flow diagram of FIG. 17, contacting at least a portion of the major surface of the battery with the ridge (300) and forming a trough between a side edge of the battery and a trough forming element of the form (320) may be performed by a single action (400).

Figure 18:
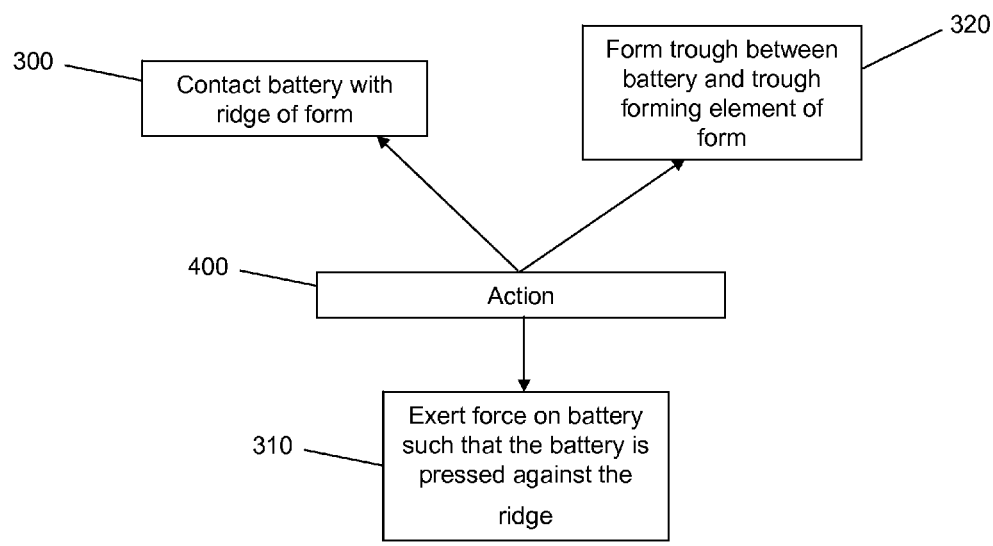

As shown in the flow diagram of FIG. 18, contacting at least a portion of the major surface of the battery with the ridge (300), exerting force on the battery such that the battery is pressed against the ridge (310) and forming a trough between a side edge of the battery and a trough forming element of the form (320) may be performed by a single action (400).

One of skill in the art will understand that components or steps described herein regarding a given embodiment or set of embodiments may readily be omitted, substituted, or added from, with, or to components or steps of other embodiments or sets of embodiments, as appropriate or desirable.

Thus, embodiments of FORM FOR RETAINING BATTERY IN IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A form for retaining a battery of an implantable medical device, the battery having first and second opposing major surfaces and an edge surface connecting the first and major surfaces, the form comprising:
   an outer edge;
   first and second opposing major surfaces,
      the first major surface including a recess, a ridge disposed between the recess and the outer edge, and a trough forming element disposed between the ridge and the outer edge,
      the ridge configured to engage at least a portion of the first major surface of the battery retained in the form,
      the trough forming element having first and second edge surfaces positioned to engage the edge surface of the retained battery to form a trough configured to receive adhesive,
      the recess disposed adjacent the ridge and being configured to allow for expansion of the retained battery during recharge; and
   a retention assembly configured exert force on the second major surface of the battery such that the opposing first major surface of the battery is pressed against the ridge to prevent adhesive from leaking from the trough into the recess.

2. The form of claim 1, wherein the retention assembly is secured relative to the first major surface of the form.

3. The form of claim 1, wherein the retention assembly is formed from the first major surface of the form.

4. The form of claim 3, wherein the retention assembly comprises first and second engagement members,
   the first engagement member having a wall and an engagement feature, wherein the engagement feature is secured relative to the wall and is positioned to engage a first portion of the second major surface of the battery,
   the second engagement member having a wall and an engagement feature, wherein the engagement feature is secured relative to the wall and is positioned to engage a second portion of the second major surface of the battery,
   wherein the wall of the first engagement feature and the wall of the second engagement feature are generally opposed.

5. The form of claim 1, wherein the ridge defines the outer edge of the recess.

6. The form of claim 1, wherein the first major surface further comprises a region configured to receive electronic circuitry.

7. The form of claim 6, further comprising a plurality of pins for electrically coupling the circuitry to a recharge coil, the pins being received in and protruding from the first major surface of the form.

8. The form of claim 7, wherein the pins are molded into the form.

9. The form of claim 1, wherein the second major surface of the form is configured to receive a recharge coil.

10. The form of claim 9, wherein the second major surface of the form includes a recessed portion configured to receive the recharge coil.

11. The form of claim 10, wherein the second major surface of the form includes a raised portion, around which the recessed portion is disposed.

12. An implantable medical device comprising:
a housing;
electronics disposed in the housing;
the form of claim 9 disposed in the housing;
a battery retained in the form and operably coupled to the electronics;
a recharge coil retained in the housing and operably coupled to the battery.

13. An implantable medical device comprising:
a housing;
electronics disposed in the housing;
the form of claim 1 disposed in the housing;
a battery retained in the form and operably coupled to the electronics;
a recharge element operably coupled to the battery.

14. A method for securing a battery in a form for insertion in a medical device, the form having an outer edge, a recess, and a ridge disposed between the outer edge and the recess, the method comprising:
contacting at least a portion of a major surface of the battery to the ridge;
pressing the at least a portion of the major surface of the battery against the ridge,
wherein pressing the battery comprises exerting force via an engagement feature of the form;
forming a trough between a side edge of the battery and a trough forming element of the form; and
placing adhesive in the trough,
wherein the battery is pressed against the ridge with sufficient force to prevent the adhesive from leaking from the trough into the recess.

15. The method of claim 14, wherein a single action results in (i) contacting the major surface of the battery to the ridge and (ii) forming a trough between a side edge of the battery and a trough forming element of the form.

16. The method of claim 14, wherein a single action results in (i) contacting the major surface of the battery to the ridge, (ii) exerting force on the battery such that the battery is pressed against the ridge, and (iii) forming a trough between a side edge of the battery and a trough forming element of the form.

17. The method of claim 14, wherein contacting the major surface of the battery to the ridge comprises contacting a major surface of a rechargeable battery to the platform element.

* * * * *